United States Patent [19]

Robins et al.

[11] 4,328,336

[45] May 4, 1982

[54] 9-(β-D-RIBOFURANDSYL)PURINE-6-CARBOXAMIDE AND RELATED COMPOUNDS

[75] Inventors: Roland K. Robins, Provo, Utah; Robert J. Rousseau, Laguna Niguel, Calif.

[73] Assignee: ICN Pharmaceuticals, Inc., Covina, Calif.

[21] Appl. No.: 181,635

[22] Filed: Aug. 26, 1980

[51] Int. Cl.³ .................... C07H 19/20; C07H 19/18; C07H 19/16

[52] U.S. Cl. ........................ 536/28; 536/24; 536/26; 536/27

[58] Field of Search ............... 536/24, 26–28; 424/180

[56] References Cited

U.S. PATENT DOCUMENTS 3,480,613 11/1969 Walton .................................. 536/24
3,803,126 4/1974 Rousseau et al. ..................... 536/24

OTHER PUBLICATIONS

Chemical Abstracts, vol. 68, p. 1289, 1968, Abst. No. 13312g, "Non Catalytic Fusion Reaction of 1,2,3,5, tetra–O–acetyl–β–D–ribofuranose With Purine Derivatives.

Westover, J. D., et al., Division of Medicinal Chemistry, Second Chemical Congress of the North American Continent, Aug. 25–29, 1980, Abstract No. 20.

Sidwell, Robert et al., Applied Microbiology, vol. 22, pp. 797–801, 1971.

Ishido, Y., et al., Bull. Chem. Soc. Jap., vol. 40, pp. 1007–1009, 1967.

*Primary Examiner*—Blondel Hazel
*Attorney, Agent, or Firm*—K. H. Boswell

[57] ABSTRACT

Certain 9-(β-D-Ribofuranosyl)purine-6-carboxamide and other related compounds are prepared and are useful as antiviral agents.

7 Claims, No Drawings

9-(β-D-RIBOFURANDSYL)PURINE-6-CARBOXA-MIDE AND RELATED COMPOUNDS

BACKGROUND OF THE INVENTION

Certain 9-(β-D-Ribofuranosyl) 6-substituted purines including the carboxamide, the thiocarboxamide and the carbonitrile are prepared and certain of these have been tested and found to have biological activity as an antiviral agent while others are useful as precursors in forming the biologically active compounds.

Over the last three decades medical science has discovered and learned to use chemotherapeutic agents having activity against microorganisms including bacterium and certain fungi. Excluded from this group have been agents which are active against viruses.

Viral infections are known to be one of the most frequent causes of human illness. Upwards of 300 different immunologic types of virus have been associated with humans; however, not all of these are identified with clinical recognizable diseases.

Many of these diseases, having once been acquired, render their host free from further infections by the same agent by stimulating a life-long immunologic response by the host to the viral agent. It is by this very same mechanism that conquest of certain virus-caused disease states has been achieved. By using prophylaxis induced by either killed or attenuated viruses or infection with an immunologically related virus which causes a very mild disease state, vaccines have been developed, for smallpox, yellow fever, polio, and some of the common childhood diseases, e.g. mumps, rubella, and measles.

While prophylaxis from some viral diseases can be obtained by immunity, immunologic protection from other viural diseases is not possible because either prolonged immunity is not developed against the virus, or the same clinically described disease is caused by a large group of related viruses which are antigenically dissimilar and do not produce cross immunity, e.g. common cold viruses. Coupled with this lack of universal prophylaxis against all viral diseases is the necessity to effect a cure in an already established viral disease.

In the last few years research has been centered on finding effective chemotherapeutic antiviral agents. At present there are only a very few compounds known to be active against viruses. Included in this group are amantadine(1-adamantanamine), methisazone(1-methylisatin B-thiosemicarbazone), cytarabine (cytarabine (cytosine arabinoside), 6-IDU (5-iodo-2'-deoxyuridine); however, these agents are of either limited spectrum, e.g., amantadine is only active against Type A influenze virus, cytarabine and 5-IDU are not active against RNA viruses and they are quite toxic.

BRIEF SUMMARY OF THE INVENTION

Certain purine 9-β-D-Ribofuranosyl nucleosides and nucleotides are known to be constituents of many biological compounds including RNA, DNA, part of the energy transport system of ATP as well as the intercellular regulatory system of cyclic AMP. With the possible exception of the 6-chloro derivative, which is quite toxic, little or no antiviral activity has thus far been associated with any purine 9-β-D-Ribofuranosyl nucleosides or nucleotides.

The present invention is directed to certain derivatives of the purine 9-β-D-Ribofuranosyl system which have been shown to have significant antiviral activity. Included in this group are the 6-carbonitrile(6), the 6-carboxamide(3) and the 6-thiocarboxamide(9) 9-β-D-Ribofuranosyl purines. The sugar moiety of the basic nucleoside can be appropriately blocked with suitable acyl blocking groups, preferredly $C_1$-$C_{18}$ acyl. Additionally, the 5' phosphate(4) of the 6-carboxamide(3) was prepared.

The group of compounds are compounds of the structure

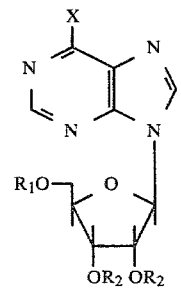

wherein X is

or C≡N, R is O or S, $R_1$ is H, Ac or $PO(OH)_2$, $R_2$ is H or Ac and Ac is $C_1$-$C_{18}$ acyl, with the proviso that when X is C≡N, $R_1$ and $R_2$ are not Ac.

The formation of any carbon-carbon bond at the 6-position of purine nulecosides through nucleophilic displacement of the corresponding 6-chloropurines has been generally unsuccessful. The preparation of purine nucleosides having carbon substitution at the 6-position has therefore generally only been obtained by glycosylation of appropriate purine bases containing a preformed carbon-carbon bond at the 6-position. The 6-carboxamide compound(3) of the invention is prepared by both of the above two mentioned routes, (a) nucleophilic displacement on a preformed nucleoside and (b) glycosylation of purine-6-carboxamide(1). When the 6-carboxamide compound(3) is prepared via nucleophilic displacement, purine-6-carboxamide(1) is appropriately blocked with the trimethylsilyl blocking group followed by coupling with a suitable acyl block 9-β-D-Ribofuranose in the presence of a Lewis acid. This leads to an appropriate acyl blocked nucleoside 9-(2,3,5-tri-O-acyl-β-D-Ribofuranosyl)purine-6-carboxamide(2). Appropriate deacylation yields 9-(β-D-Ribofuranosyl)purine-6-carboxamide(3). Alternately this same compound can be formed via a 6-carbonitrile intermediate as outlined in the next paragraph.

The above mentioned 6-carbonitrile(6) compound represents a carbon-carbon bond formation at the 6-position of the purine moiety. This is achieved by treating 9-(β-D-Ribofuranosyl)-6-iodopurine(5) with CuCN in pyridine. Treatment of the 6-carbonitrile compound(6) with $H_2O_2$ in alkaline media yields the above noted 6-carboxamide compound. The 6-carboxamide compound is identical when prepared by either of the above two roots.

Compound 9-(β-D-Ribofuranosyl)purine-6-carboxamide can be directly phosphorylated with $POCl_3$ in trimethylphosphate followed by hydrolysis to give 9-

(β-D-Ribofuranosyl)purine-6-carboxamide 5'-phosphate(4).

A blocked 6-carbonitrile purine nucleoside is known, see Y. Ishido, T. Matsuba, A. Hosono, K. Fugii, T. Sato, S. Isome, A. Maruyama, and Y. Kikuchi, *Bull. Chem. Soc.*, (Japan), 40, 1007 (1967). This compound 9-(2,3,5-tri-O-acyl-β-D-Ribofuranosyl)purine-6-carbonitrile(7) can be appropriately treated with $H_2S$ in pyridine to yield 9-(2,3,5-tri-O-acyl-β-D-Ribofuranosyl)2-purine-6-thiocarboxamide(8). This compound upon subsequent deacylation furnishes 9-β-D-ribofuranosyl-purine-6-thiocarboxamide(9).

While the nucleotide compound 4 was isolated as the free acid it could also be prepared as an acceptable physiological salt. Acceptable salts can be selected from but are not necessarily limited to the group consisting of alkali and alkaline earths, e.g., sodium, potassium, calcium, magnesium, lithium, ammonium and substituted ammonium, trialkylammonium, dialkylammonium, alkylammonium, e.g., triethylammonium, trimethylammonium, diethylammonium, octylammonium, cetyltrimethylammonium, cetylpyridium. The hydroxyl groups of the nucleoside compounds 3 and 9 can be blocked with $C_1$-$C_{18}$ acyl groups. These groups can be selected from a group consisting of straight chain, branched chain, substituted, unsaturated, saturated or aromatic acid such as, but not necessarily limited to, acetic, trifluoroacetic, propionic, n-butyric, isobutyric, valeric, caproic, pelargonic, enanthic, capyrlic, latic, acrylic, propargylic, palmitic, benzoic, phthalic, salicyclic, cinnamic and naphthoic acids. A more preferred acyl blocking group would be $C_1$-$C_8$ acyls members of the above group.

Antiviral activity of the compounds of the invention was determined both in vitro and in vivo. In vivo activity was determined utilizing either the virus induced cytopathic effect CPE as an indicator or plaque inhibition. The CPE method has been reported by R. W. Sidwell and J. H. Huffman, *Appl. Microbiol.*, 22, 797 (1971). The procedure of the CPE test and the results are shown in example 7 and Table I. For comparison purposes the known antiviral 1-(β-D-Ribofuranosyl)-1,2,4-triazole-3-carboxamide (Ribavirin) is also shown in Table I. The plaque inhibition test is shown in example 8 and Table II while the in vivo test is shown in example 9.

It is known that the antiviral compound 1-(β-D-Ribofuranosyl)-1,2,4-triazole-3-carboxamide (riboviran) also exhibits its antiviral effect in vivo when delivered as the 5'nucleotide. In fact it is even speculated that in vivo this compound is metabolically elevated to the 5'nucleotide form before it expresses its antiviral effect. Similarly this same compound riboviran can be converted to a pro drug form by acetylated or otherwise making it more lipid soluble by blocking its hydroxyl groups appropriately. Such a lipid form of a compound encourages better absorption into certain body organs and/or cells which are basically more lipid-like in nature. For these reasons the 5'phosphate form of compound 3 is expected to have significant in vivo activity. Additionally to facilitate absorption into more lipid environments in vivo acylated forms of the compounds might be preferred. Either of these forms therefore could be considered as pro drugs to facilitate delivery and/or expression in vivo.

BACKGROUND OF THE INVENTION

The compounds of the invention were prepared as per the following examples. For use in preparing the compounds for the invention purine-6-carboxamide(1) was prepared as per L. B. Mackay and G. H. Hitchings, *J. Am. Chem. Soc.*, 78, 3511 (1956). 9-(β-D-Ribofuranosyl)-6-iodopurine was prepared as per J. F. Gerster, J. W. Jones, and R. K. Robins, *J. Org. Chem.*, 28, 945 (1963). 9-(2,3,5-tri-O-acetyl-β-D-Ribofuranosyl)purine-6-carbonitrile(7) was prepared as per Y. Ishido, T. Matsuba, A. Hosono, K. Fugii, T. Sato, S. Isome, A. Maruyama, and Y. Kikuchi, *Bull. Chem. Soc.*, (Japan), 40, 1007 (1967).

For all compounds melting points were taken on a Thomas-Hoover capillary melting point apparatus and are uncorrected. Nuclear magnetic resonance ($^1$H NMR) spectra were determined at 90 MHz with Varian EM-390 spectrometer. The chemical-shift values are expressed in δ values (ppm) relative to tetramethylsilane as an internal standard. The presence of $H_2O$ or EtOH as indicated by elemental analyses was verified by $^1$H NMR. Infrared spectra (IR) were obtained on a Perkin-Elmer 257 spectrophotometer (KBr pellets) and ultraviolet spectra (UV, sh-shoulder) were recorded on a Cary Model 15 spectrophotometer. Elemental analyses were obtained for all compounds and except as otherwise noted for compound 4 the results are within ±0.4% of the theoretical values. Thin-layer chromatography (tlc) was run on silica gel 60 F-254 (EM Reagents) plates. ICN Woelm silica gel (70–230 mesh) was used for column chromatography and $EtOAc:H_2O:1$-PrOH, 4:2:1, upper phase, as the eluting solvent. All solvents used were reagent grade. Detection of components on tlc was by uv light and with 10% $H_2SO_4$ in MeOH spray followed by heating. Evaporations were carried out under reduced pressure with the bath temperature below 30° C.

EXAMPLE 1

9-(2,3,5-Tri-O-benzoyl-β-D-ribofuranosyl)purine-6-carboxamide(2)

A mixture of dry purine-6-carboxamide(1) (2.44 g, 15 mmol, dried at 110° C. over $P_2O_5$ under vacuum, overnight), freshly distilled hexamethyldisilazane (HMDS, 15.0 mL) and a few crystals of $(NH_4)_2SO_4$ (25 mg) was heated at reflux temperature for 18 h under anhydrous conditions. The excess HMDS was removed by distillation and the residual solid was presumed to be trimethylsilyl (TMS) derivative and was used without further purification. To a solution of the TMS derivative in dry 1,2-dichloroethane (100 mL) was added 1-O-acetyl-2,3,5-tri-O-benzyl-β-D-ribofuranose (7.56 g, 15 mmol) followed by anhydrous $SnCl_4$ (5.47 g, 21 mmol). The reaction mixture was protected from moisture and stirred at ambient temperature for 24 h. The mixture was poured into a cold mixture of 5% aqueous $NaHCO_3$ (600 mL) and $CHCl_3$ (250 mL), and stirred for 2 h. The resulting emulsion was filtered through a Celite pad, the filter cake was washed well with $CHCl_3$ (5×50 mL). The combined organic layer was washed with 5% aqueous $NaHCO_3$ (2×100 mL) followed by water (2×100 mL) before it was dried over anhydrous $Na_2SO_4$. Removal of $CHCl_3$ gave a solid residue which was triturated with ether, filtered and air dried. Crystallization from EtOH gave 7.58 g (83.2%) of pale yellow needles; mp 194°–195° C.; $^1$H NMR ($Me_2SO$-$d_6$) δ 6.82

(d,1,J=5.0 Hz, $C_1$,H), 8.03 and 8.36 (2s,2,$CONH_2$), 8.93 and 9.06 (2s,$C_2H$ and $C_8H$), and other sugar protons; IR 1690 (amide C=O), 1720 (C=O), 3300 and 3400 (amide $NH_2$) cm$^{-1}$; UV λmax (pH 1) 235 nm (ε 30,300), 277 (12,700); λmax (pH 7) 235 nm (ε 27,700), 277 (12,700); λmax (pH 11) 233 nm (ε 34,000), 277 (11,200). Anal. ($C_{32}H_{25}N_5O_8$) C, H, N.

EXAMPLE 2

9-(β-D-Ribofuranosyl)purine-6-carboxamide(3)

Method 1

To a solution of 2 (6.07 g, 10 mmol) in anhydrous MeOH (100 mL) was added NaOMe till the pH was 8.5 and the mixture was stirred at ambient temperature for 15 h with the exclusion of moisture. The reaction mixture was neutralized with Amberlite IRC-50. The resin was removed by filtration and washed with hot MeOH (3×35 mL). The combined filtrates were evaporated to dryness. The residue was dissolved in minimum amount of water and precipitated by addition of EtOH. Crystallization of the precipitate from large excess of EtOH gave colorless crystals, 2.8 g (94.8%); mp 110°–112° C. (dec); $^1$H NMR ($Me_2SO$-$d_6$) δ 6.12 (d,1,J=5.5 Hz, $C_1$,H), 8.06 and 8.38 (2s,2, $CONH_2$, exchanged with $D_2O$), 9.02 and 9.06 (2s, $C_2H$ and $C_8H$), and other sugar protons; IR 1690 (amide C=O), 3350 (amide $NH_2$,OH) cm$^{-1}$; UV λmax (pH 1,7 and 11) 282 nm (ε 7,900). Anal. ($C_{11}H_{13}N_5O_5$·$H_2O$) C, H, N.

Method 2

To a suspension of 9-(β-D-ribofuranosyl)purine-6-carbonitrile 6 (0.5 g, 1.8 mmol) in 50% aqueous MeOH (50 mL), cooled to −10° C., was added conc $NH_4OH$ (or 10% NaOH) till the pH was 8.5. 30% $H_2O_2$ (0.4 mL, 3.6 mmol) was added and stirred for 2 h. The mixture was evaporated to dryness and purified by column chromatography to yield 0.30 g (56.5%). This material was identical with 3 prepared by method 1.

EXAMPLE 3

9-(β-D-Ribofuranosyl)purine-6-carboxamide 5′-phosphate(4)

A solution of phosphoryl chloride (1.0 mL) in trimethylphosphate (20 mL) was cooled to 0° C., and 3 (1.0 g, 3.38 mmol) was added with stirring. The mixture was protected from moisture and stirred for 5 h at 0° C. until phosphorylation was complete, as shown by tlc of a hydrolyzed aliquot on silica gel with $CH_3CN$-0.1 N $NH_4Cl$ (7:3) as developer. The solution was poured into ice-water (40 mL) and the pH was adjusted to 2 with 2 N NaOH. The solution was extracted with $CHCl_3$ (2×50 mL) to remove trimethylphosphate. The aqueous solution was applied to a column of activated charcoal (30 g), and the column was washed with $H_2O$ until the eluate was salt free. The nucleotide was eluted with a mixture of EtOH-$H_2O$-conc $NH_4OH$ (10:10:1,v/v). The solvent was removed and the residue was dissolved in $H_2O$ (20 mL). This aqueous solution was passed through a column of Bio-Rad AG 50W-X2 (H+). Elution with $H_2O$ afforded the nucleotide. The solvent was removed and the residue was dissolved in $H_2O$ (10 mL), frozen, and lyophilized to yield 0.66 g (52.0%) of the nucleotide, mp 118°–125° C. (dec); $^1$H NMR ($Me_2SO$-$d_6$) δ 6.12 (d,1,J=6.0 Hz, $C_1$,H), 8.03 and 8.33 (broad, 2s, $CONH_2$, exchanged with $D_2O$), 8.90 and 9.03 (2s, $C_2H$ and $C_8H$), and other sugar protons; IR 1685 (amide C=O), 3310–3400 (OH) cm$^{-1}$; UV λmax (pH 1) 279 nm (ε 7,500); λmax (pH 7 and 11) 282 nm (ε 7,600). Anal. ($C_{11}H_{14}N_5PO_8$·$H_2O$) C, H, N, P.

In spite of duplicate analysis it was difficult to get correct nitrogen analysis, presumably because of incomplete combustion. All spectral data, however, are consistent with the assigned structures. Nitrogen analysis was calculated to be 17.80 and found to be 17.18. Carbon, hydrogen and phosphorus analysis was within the 0.4% range, however.

EXAMPLE 4

9-(β-D-Ribofuranosyl)purine-6-carbonitrile(6)

A mixture of CuCN (5.0 g, 55 mmol) and dry pyridine (75 mL) was heated under reflux with the exclusion of moisture. The solution was cooled to room temperature as 9-(β-D-ribofuranosyl)-6-iodopurine(5) (5.0 g, 13.2 mmol) was added. The mixture was heated again to reflux temperature for 5 min and then evaporated to dryness. The black residual solid was triturated with $H_2O$ (3×50 mL), followed by EtOH (3×50 mL). The combined $H_2O$ and EtOH extracts were evaporated to dryness along with silica gel (10 g). The crude product which had been absorbed onto silica gel was loaded onto a 3×25 cm silica gel column packed in EtOAc and eluted with EtOAc: $H_2O$:1-PrOH (4:2:1, upper phase). The appropriate fractions were collected, solvent evaporated to yield 2.2 g (60.0%) of tan colored solid. Crystallization from EtOH gave the product as light tan colored needles, mp 198°–199° C. (dec); $^1$H NMR ($Me_2SO$-$d_6$) δ 6.08 (d,1, J=6.0 Hz, $C_1$,H), 9.12 and 9.15 (2s, $C_2H$ and $C_8H$), and other sugar protons; IR 2240 (C≡N, very weak), 3380 (OH) cm$^{-1}$; UV λmax (pH 1 and 7) 286 nm (ε 9,700); λmax (pH 11) 284 nm (e 7,800), 320 sh (3,000). Anal. ($C_{11}H_{11}N_5O_4$) C, H, N.

EXAMPLE 5

9-(2,3,5-Tri-O-Acetyl-β-D-ribofuranosyl)purine-6-thiocarboxamide(8)

$H_2S$ gas was bubbled through a solution of 9-(2,3,5-tri-O-acetyl-β-D-ribofuranosyl)purine-6-carbonitrile(7) (4.03 g, 10 mmol) in anhydrous pyridine (250 mL) at room temperature, with stirring, until the deep color which had formed began fading. Stirring was continued for further 2 h before the amber colored solution was flushed with $N_2$. Evaporation of the mixture gave a syrup which on crystallization with 2-propanol containing a few drops of pet. ether (30°–60° C.) afforded 3.87 g (88.5%) of light orange crystals, mp 154.5°–155° C.; $^1$H NMR ($Me_2SO$-$d_6$) δ 6.43 (d,1,J=6.0 Hz, $C_1$,H), 8.93 and 9.06 (2s, $C_2H$ and $C_8H$), 10.03 and 10.60 (2s, $CSNH_2$, exchanged with $D_2O$), and other sugar protons; IR 1220

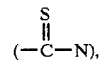

1740 (C=O), 3300 (amide NH) cm$^{-1}$; UV λmax (pH 1 and 7) 280 nm (ε 8,000), λmax (pH 11) 273 nm (ε 7,600). Anal. ($C_{17}H_{19}N_5SO_7$) C, H, N, S.

EXAMPLE 6

9-(β-D-Ribofuranosyl)purine-6-thiocarboxamide(9)

A solution of 8 (1.0 g, 2.28 mmol) in cold (0° C.) MeOH (80 mL) was saturated with $NH_3$ and allowed to stand in a pressure bottle at 5° C. for 20 h. The MeOH/NH₃ was evaporated to dryness and the residual solid triturated with boiling benzene (5×25 mL). The benzene insoluble solid was crystallized from 2-propanol to yield 0.35 g (49.3%) of light tan needles, mp 167°–169° C. (dec). $^1$H NMR (Me₂SO-d₆) δ 6.50 (d,l,J=5.0 Hz, C₁,H), 8.8 and 9.0 (2s, C₂H and C₈H), 10.1 and 10.5 (2s, CSNH₂, exchanged with D₂O), and other sugar protons; UV λmax (pH 1) 280 nm (ε 10,000); λmax (pH 7) 280 nm (ε 8,500); λmax (pH 11) 272 nm (ε 7,800). Anal. (C₁₁H₁₃N₅SO₄) C, H, N.

EXAMPLE 7

Antiviral Evaluation

Inhibition of the virus-induced cytopathic effect (CPE) was used as the initial indicator of antiviral activity. CPE was observed in African green monkey kidney (Vero, V) and the human laryngeal epithelioma (HEp-2, H) cells after infection with herpes simplex type 1 (HSV 1), vaccinia (vv), parainfluenza type 3 (para 3), vesicular stomatitis (vsv) and coxsackie type B1 (cox B1) viruses. In this system, monolayers (18 h) of cells were exposed to 320 CCID₅₀ of virus and concentrations of each compound ranging in one-half log dilutions from 1000 to 1 μg/ml were added within 15 min. The degree of CPE inhibition and compound cytotoxicity were observed microscopically after 72 h of incubation at 37° in 5% CO₂ and scored numerically in order to calculate a virus rating (VR) as per the Sidwell procedure noted above. Significance of antiviral activity in terms of VR's has been assigned as follows: 0.5, slight or no activity; 0.5–0.9, moderate activity; and ≧1.0 marked activity. Compounds 3, 9, and 6 showed significant antiviral activity as shown in a parallel experiment with 1-(β-D-Ribofuranosyl)-1,2,4-triazole-3-carboxamide (Ribavirin) as shown in Table I. Compounds 3 and 10 exhibited marked antiviral activity against both RNA and DNA viruses in cell culture depending on the cell line.

EXAMPLE 8

For plaque inhibition 9-(β-D-Ribofuranosyl) purine-6-carboxamide(3) was tested at the U.S. Army Medical Research Institute of Infectious Diseases, Fort Detrick, Md., against Rift valley fever (RVF) and Pichinde (PICH) viruses in vitro in vero cells. The inhibition of viral growth by compound 3 at various concentrations in cell culture is shown in Table II. It inhibited the RVG virus growth to the extent of 90% at 250 μg/ml. Similarly compound 3 also inhibited PICH virus to the extent of 90% at 250 μg/ml.

EXAMPLE 9

In an in vivo study compound 3 was employed in the treatment of RVF virus infected mice. At 50 mg/kg/day compound 3 gave a 55% survival rate on day 21 compared to a 30% survival in the controls.

TABLE I

Comparative in Vitro Antiviral Activity of Ribavirin and Certain 9-(β-D-Ribofuranosyl)purine-6-carboxamides

| No. | Compd. | cell line/ toxic level | Virus Ratings[a] | | | | |
|---|---|---|---|---|---|---|---|
| | | | HSV1 | VV | Para 3 | VSV | Cox B1 |
| 3 | 9-(β-D-Ribofuranosyl)purine-6-carboxamide | V/none | 0.6 | 1.5 | 0.0 | 0.0 | 0.4 |
| | | H/320 | 0.6 | 1.1 | 1.4 | 1.2 | 0.9 |
| 9 | 9-(β-D-Ribofuranosyl)purine-6-thiocarboxamide | V/320 | 1.1 | 0.8 | b | 0.5 | 1.0 |
| | | H/100 | 0.4 | 1.2 | 1.3 | 0.7 | 1.1 |
| 6 | 9-(β-D-Ribofuranosyl)-6-cyano-purine | V/1000 | 0.4 | 1.0 | 0.0 | 0.0 | 0.0 |
| | | H/320 | 0.8 | 1.0 | 1.2 | 0.8 | 1.0 |
| | 1-(β-D-Ribofuranosyl)-1,2,4-triazole-3-carboxamide (Ribavirin) | V/none | 0.6 | 1.2 | 1.3 | 0.8 | 0.6 |
| | | H/none | 1.2 | 1.2 | 1.4 | 1.6 | 1.1 |

The virus rating (VR) was determined by comparing CPE development in drug-treated cells (T) and virus control cells (C). The CPE value (0–4) assigned to T for each drug level was subtracted from that of C and the differences (C −T) were totaled. If partial toxicity was evident at any drug level, the C −T of that level was divided by 2. The sum of all C −T values was then divided by ten times the number of test cups used per drug level.

TABLE II

Inhibition of viral growth by 9-(β-D-Ribofuranosyl) purine-6-carboxamide(3)

| CONCENTRATION | % PLAQUE REDUCTION | |
|---|---|---|
| μg/ml | RVFV | PICH |
| 25 | ≈10% | ≈25% |
| 100 | — | ≈50% |
| 250 | ≈90% | ≈90% |
| 500 | ≈98% | ≈95% |

RVFV - Rift Valley Fever virus in Vero cells
PICH - Pichinde virus in Vero cells

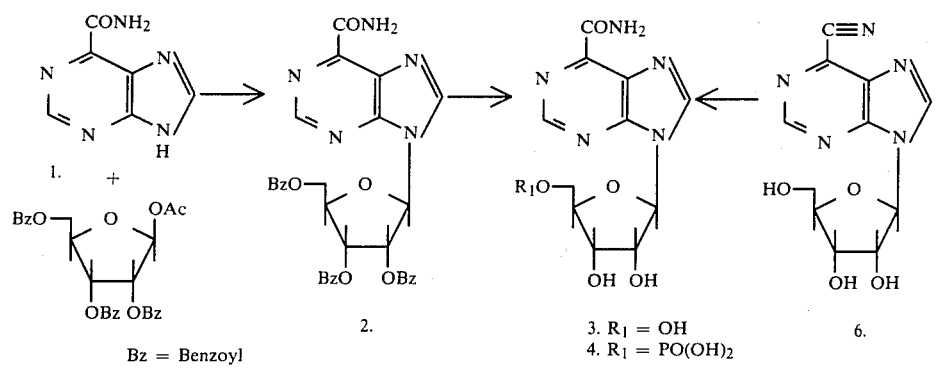

-continued

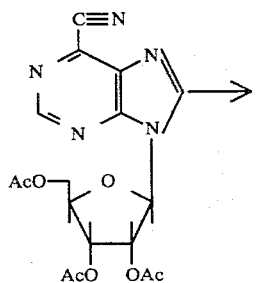 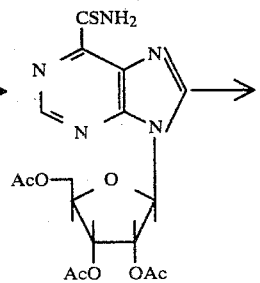 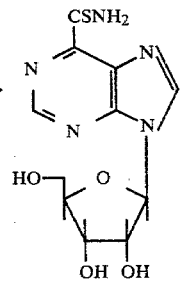 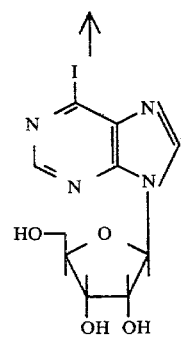

7.   8.   9.   5.

We claim:
1. A compound of the structure:

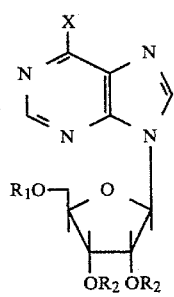

wherein X is

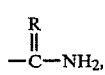

R is O or S, R₁ is H, Ac or PH(OH)₂, R₂ is H or Ac and Ac is C₁–C₁₈ acyl.

2. A compound of claim 1 wherein:
R is O.
3. A compound of claim 1 wherein:
R is S.
4. A compound of claim 1 wherein:
X is $$\overset{R}{\underset{\|}{C}}-NH_2,$$

R is O and R₁ is PO(OH)₂.
5. a compound of claim 1 wherein:
X is $$\overset{R}{\underset{\|}{C}}-NH_2$$

and R₁ and R₂ are Ac.
6. A compound of claim 5 wherein:
R is O.
7. A compound of claim 6 wherein:
Ac is benzoyl.

* * * * *